United States Patent [19]

Botteghi et al.

[11] 4,438,033
[45] Mar. 20, 1984

[54] STEROIDAL CHIRAL PHOSPHINES, METHODS FOR THEIR PREPARATION, CATALYTIC SYSTEMS CONTAINING THEM AND CATALYTIC PROCESSES IN WHICH THEY ARE USED

[75] Inventors: Carlo Botteghi, Alghero; Serafino G. Gladiali, Sassari; Mauro Marchetti, Sassari; Giovanni A. Faedda, Sassari, all of Italy

[73] Assignee: Consiglio Nazionale Delle Ricerche, Rome, Italy

[21] Appl. No.: 442,679

[22] Filed: Nov. 18, 1982

[30] Foreign Application Priority Data

Dec. 4, 1981 [IT] Italy ............................. 25463 A/81

[51] Int. Cl.³ .............................................. C09J 21/00
[52] U.S. Cl. ........................... 260/239.55 C; 260/397.2
[58] Field of Search .................... 260/239.55 C, 397.2; 252/426

[56] References Cited

PUBLICATIONS

Chem. Abstract, vol. 90, 1979, p. 587, 90:22346c.
Chem. Abstract, vol. 92, 1980, p. 571, 92:6067y.
Chem. Abstract, vol. 82, 1975, p. 571, 171186n.
Chem. Abstract, vol. 83, 1975, p. 571, 164367q.
Chem. Abstract, vol. 86, 1977, p. 662, 86:190463z.
Chem. Abstract, vol. 86, 1977, p. 574, 86:189565c.
Chem. Abstract, vol. 87, 1977, p. 449, 87:5591z.
Chem. Abstract, vol. 89, 1978, p. 713, 89:44226v.
Chem. Abstract, vol. 89, 1978, p. 646, 89:180371r.
Chem. Abstract, vol. 77, 1972, p. 467, 114567k.
Chem. Abstract, vol. 81, 1974, p. 395, 90644n.
Chem. Abstract, vol. 82, 1975, p. 496, 86086k.
Chem. Abstract, vol. 86, 1977, p. 641, 86:72920y.
Chem. Abstract, vol. 86, 1977, p. 337, 86:29501a.
Chem. Abstract, vol. 85, 1976, p. 594, 85:123336b.
Chem. Abstract, vol. 88, 1978, p. 554, 88:6562y.

*Primary Examiner*—Elbert L. Roberts
*Attorney, Agent, or Firm*—Stevens, Davis, Miller & Mosher

[57] ABSTRACT

New steroidal chiral phosphines of formula

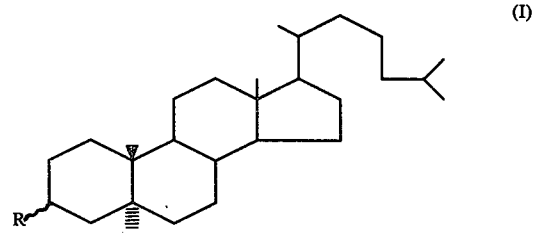

(I)

wherein R represents a phosphorated group selected between

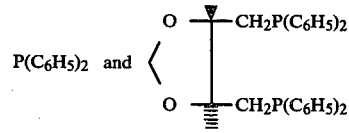

methods for their preparation; catalytic systems comprising metal complexes and the above steroidal chiral phosphines; asymmetrical catalytic processes like hydrogenation, hydroformylation and hydrocarbalkoxylation of prochiral compounds which employ said catalytic systems.

5 Claims, No Drawings

STEROIDAL CHIRAL PHOSPHINES, METHODS FOR THEIR PREPARATION, CATALYTIC SYSTEMS CONTAINING THEM AND CATALYTIC PROCESSES IN WHICH THEY ARE USED

DESCRIPTION OF THE INVENTION

The present invention refers to new steroidal chiral phosphines, to methods for their preparation, to catalytic systems comprising metal complexes and the above steroidal chiral phosphines and to asymmetrical catalytic processes like hydrogenation, hydroformylation and hydrocarbalkoxylation of prochiral compounds which employ said catalytic system. More precisely, one object of the present invention is represented by new steroidal phosphines, chiral to the carbon atom, of the general formula

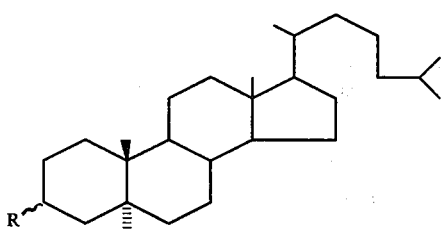

wherein R is a phosphorated group selected between

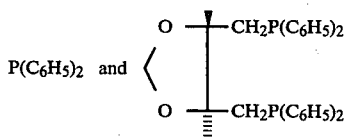

In the patent literature there are described many phosphines which are used as ligands in catalysts suitable for asymmetric synthesis like asymmetric hydroformylation, asymmetric hydrogenation, asymmetric hydrocarbalkoxylation and asymmetric hydrosilylation which can be useful in the synthesis of many aminoacids, drugs and pesticides.

German laid open applications Ser. Nos. 2,161,200 and 2,638,071, U.S. Pat. Nos. 4,008,281 and 4,005,127, Japanese laid open applications Ser. Nos. 76 88,942 and 78 105,421, describe many phosphines which are used as ligands in catalytic processes for asymmetric synthesis. Processes regarding other asymmetric synthesis in which chiral phosphines are used are also described in German laid open applications Ser. Nos. 2,359,101, 2,613,817, 2,638,072, 2,638,070, 2,727,671, 2,800,461, 2,909,041, well as U.S. Pat. Nos. 3,849,480, 3,949,000, 3,978,101, 3,968,147. No one of the prior-art phosphines, however, contains any steroidal structure.

The optically active compounds have achieved an increasing importance during the last years in the field of the fine chemicals, mainly of the pharmaceutical compounds. Therefore the importance of regioselective and stereospecific synthetic processes, which allow the production, with high yields, of chiral products from organic prochiral compounds, has considerably increased.

We have now discovered that the new steroidal chiral phosphines of the present invention and, consequently, the new catalytic systems, generally bring to a much higher regioselectivity, in comparison with the known catalytic systems, in asymmetrical homogeneous catalytic processes. These catalytic systems bring, in some particularly interesting cases, beside a high regioselectivity, to a high stereospecificity thus directly producing optically pure compounds.

Moreover, these new catalytic systems allow to carry out the catalytic processes in conditions much less drastic than those usually employed.

The new steroidal chiral phosphines, which will hereinafter be referred to as "the new ligands" can be prepared in an easy and cheap way, as they are synthetized in high yields from commercially available starting compounds and easily crystallize, contrary to what generally happens with the known ligands.

Particularly the objects of the present invention are the 3α-dihenylphosphines-5α-cholestane of formula

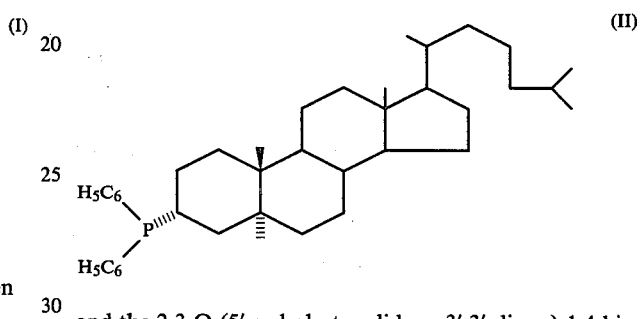

and the 2,3-O-(5'α-cholestanylidene-3',3'-dioxy)-1,4-bis-diphenylphosphinebutane of formula

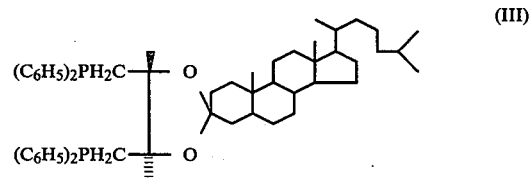

These new optically active compounds which afterwards will be referred to as (+)-DICOL (compound II) and as (−)-DIOCOL (compound III), are both prepared starting from cholesterol and sodium diphenylphosphine through a sequence of reactions.

The following reaction scheme shows the process for the synthesis of (+)-DICOL:

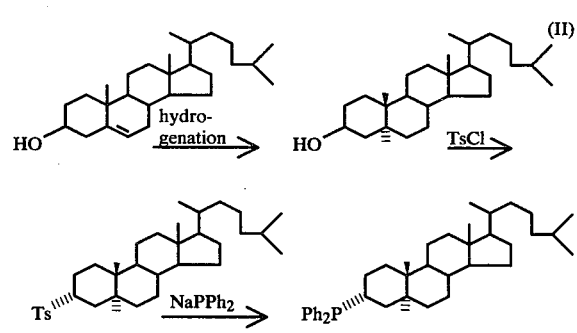

wherein TsCl means tosyl chloride and Ph stands for phenyl.

The first step, namely the reduction, is preferably carried out under hydrogen pressure in the presence of platinum as the catalyst.

The reaction of 3-hydroxycholestane with sodium diphenylphosphine is preferably carried out by first converting the 3-hydroxy-derivative into its 3-tosyl-derivative through a reaction of the 3-hydroxy-derivative with tosyl chloride in pyridine according to E. B. Hershberg et al. J. Am. Chem. Soc. 73, 1144, (1951) and J. Maunowicz et al. Chem. Listy 52, 2359, (1958).

It is also possible to protect the 3-hydroxy group with other active groups like brosyl, mesyl, triflyl, O.phthalyl, halo, acetyl or other aliphatic or aromatic ester groups.

The so obtained 5α-cholestan-3β-ol tosyl ester is reacted with sodium diphenylphosphine, which is prepared in situ from chlorodiphenylphosphine and sodium according to H. B. Kagan et al. J. Am. Chem. Soc. 94, 6429 (1972), thus obtaining in selective way the (+)-DICOL.

The reaction is carried out under nitrogen atmosphere in an anhydrous inert organic solvent like dioxane or tetrahydrofuran or a mixture thereof, preferably a 2:1 (v/v) dioxane/tetrahydrofuran mixture, at ambient temperature for a period of time comprised between 2 and 4 days, preferably 3 days. After working up the reaction mixture, (+)-DICOL is obtained with a yield never lower than 50%, in any case higher than those obtained in the synthesis of other knonw ligands like neomenthyl-phosphine or methyl-phosphine; moreover the purification does not show particular problems owing to the fact that (+)-DICOL crystallizes out from the reaction medium in an easy way.

The following reaction scheme shows the process for the synthesis of (−)-DIOCOL:

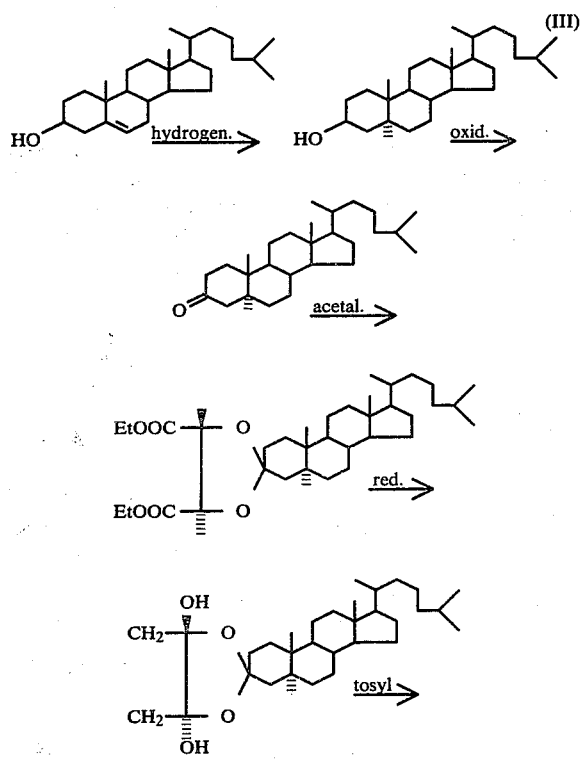

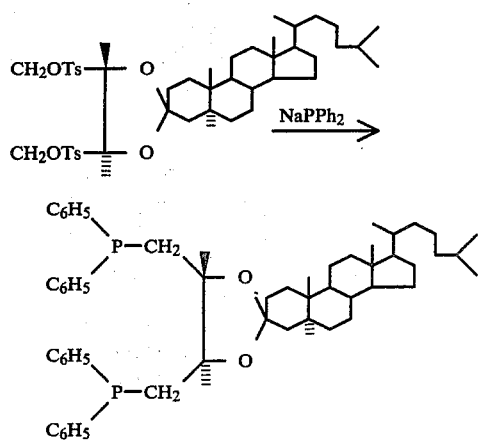

The hydrogenation of the cholesterol is preferably carried out under hydrogen pressure in the presence of platinum as the catalyst. The so obtained 5α-cholestane-3-β-ol is then oxidated to the corresponding 5α-cholestane-3-one, preferably by means of an alkali bichromate and sulphuric acid, according to L. F. Fieser and M. Fieser, Org. Synth. Coll. II, 139. The 5α-cholestane-3-one is subsequently transformed into the corresponding acetal by reaction with (R)(R)-diethyl tartrate in an organic solvent like toluene or benzene in presence of p-toluenesulfonic acid at the boiling temperature of the reaction mixture for a period of time comprised between 12 and 24 hours, preferably 18 hours. The carbethoxy groups of the resulting product are subsequently reduced to hydroxymethyl groups by means of a metal hydride such as, for instance, lithium aluminium hydride or sodium borohydride and analogs, preferably lithium aluminium hydride in anhydrous diethyl ether at the boiling temperature of the reaction mixture for a period of time comprised between 2 and 10 hours, preferably 4 hours. The so obtained 2,3-O-(5'α-cholestanylidene)-L-treitol is then transformed into the corresponding ditosyl derivative by means of tosyl chloride in pyridine. The hydroxy groups can be protected also by transforming them into the brosyl, mesyl, triflyl derivatives or into the labile esters of aromatic or aliphatic acids.

The last reaction step contemplates the introduction of the diphenylphosphinic groups by reacting the ditosyl-derivative with sodium diphenylphosphine, thus obtaining in a selective way the (−)-DIOCOL, 2,3-O-(5'α-cholestanylidene-3',3'-dioxy)-1,4-bis-diphenylphosphinebutane, with very high yields, usually higher than 90% of theoretical. This reaction is carried out by reacting 2,3-O-(5'α-cholestanylidene)-L-treitol-1,4-bis-p-tosylate with sodium diphenylphosphine under stirring at room temperature in an anhydrous inert organic solvent like dioxane or tetrahydrofuran or a mixture thereof, for a period of time comprised between 24 and 72 hours, preferably 48 hours. After working up the reaction mixture the pure (−)-DIOCOL is obtained with a yield of 90%.

The preparation of compounds (II) and (III) having a high optical purity, at least higher than 95%, is of paramount importance for the purpose of the present invention, as the presence of great quantities of other epimers alters in a determinant manner the stereoselectivity of the subsequent processes of asymmetric catalysis.

The new ligands obtained as previously described are used according to the present invention in processes of transformation of prochiral substrata into chiral compounds, by means of known catalytic precursors. The new catalytic systems are prepared in situ, by mixing the catalytic precursor together with the new ligand; subsequently the substratum is introduced and the process takes place.

Some asymmetric processes which can be carried out by means of the new catalytic systems will be hereinbelow examined in detail. This constitutes another aspect of the present invention.

A. Asymmetric hydrogenation of prochiral substrata

The hydrogenation of $\alpha,\beta$-unsaturated acids and esters is of particular interest in the field of homogeneous hydrogenations, since it brings to a number of chiral compounds which are much important for pharmaceutics and pesticides.

Processes of asymmetric hydrogenation of prochiral substrata have already been realized by using catalytic systems made by rhodium and phosphines, chiral to carbon and phosphorus atoms. The new catalytic systems of the present invention, when employed in many industrially interesting cases, like the hydrogenation of $\alpha$-acylaminoacrylic acids, allow to significantly improve the stereoselectivity of the process and thus, in this specific case, to prepare $\alpha$-aminoacids or derivatives thereof with a higher optical purity.

In a representative experiment, we have carried out the asymmetric hydrogenation of compounds of general formula:

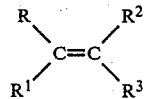

wherein R and $R^1$, independently represent hydrogen, straight or branched $(C_{1-6})$ alkyl, substituted or unsubstituted aryl, or $(C_{3-8})$ cycloalkyl; $R^1$ may be also a carboxy group; $R^2$ represents a carboxy, an ester or an amide group; $R^3$ represents $(C_{4-6})$alkyl, $(C_{3-8})$cycloalkyl a substituted or unsubstituted aryl or an amide group; in order to synthetize compounds of formula:

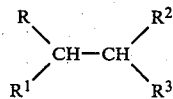

wherein R, $R^1$, $R^2$, $R^3$ are defined as above, by means of catalytic systems made by neutral or cationic monovalent rhodium complexes and ligands according to formula (I) or, more precisely, formula (II) and (III). Suitable catalytic precursors are, for instance, cyclooctadienyl-rhodium chloride dimer of formula $[Rh(COD)Cl]_2$, norbornadienyl-rhodium chloride dimer of formula $[Rh(NBD)Cl]_2$ or cationic complexes of formula $[Rh(diolefin)_2]^+ClO_4^-$, $[Rh(diolefin)_2]^+BF_4^-$, $[Rh(diolefin)_2]^+PF_6^-$.

The process is carried out in organic solvents like aromatic or aliphatic hydrocarbons, alcohols, ethers or mixture thereof, preferably a 1:1 (v/v) mixture of benzene and methanol, in the absence of air, under a hydrogen pressure comprised between 1 and 70 atmospheres, at a temperature comprised between 20° C. and 50° C. and for a period of time comprised between 12 and 24 hours. The nature of the enantiomer excess (ee) depends on the catalytic precursor, the ligand and the used substratum and cannot be foreseen a priori.

B. Asymmetric hydroformylation of prochiral substrata.

Processes of asymmetric hydroformylation with carbonmonoxide (CO) and hydrogen ($H_2$) were carried out on prochiral substrata, by using rhodium or platinum complexes as the catalysts. Nevertheless the obtained results were unsatisfactory since the optical yields were in general very low, i.e. not higher than 35%. On the other hand, in a further representative experiment it was found that by using a catalytic system comprising the art known metal complexes and the new ligands, products with the same optical yields were obtained, but a very high regioselectivity towards the formation of the chiral isomer was also achieved. The process runs according to the following scheme:

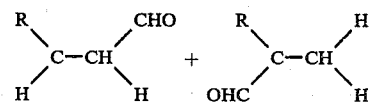

wherein R is an aliphatic straight or branched alkyl group from 1 to 20 carbon atoms or a substituted or unsubstituted aryl group.

The hydroformylation process is carried out in an autoclave by dissolving the starting material in an organic inert solvent like an aliphatic or aromatic hydrocarbon, preferably mesitylene, in presence of a catalytic amount of a ligand of formula (II) or (III) and of a metal catalyst, in the absence of air under a carbon monoxide/hydrogen pressure comprised between 70 and 100 atmospheres, being the carbon monoxide and the hydrogen present in equimolecular ratios, at a temperature comprised between 20° C. and 100° C., preferably at a temperature between 60° C. and 100° C., for a period of time comprised between 4 and 240 hours. The obtained reaction products can be purified by rectification or can be transformed into the corresponding acids by oxidation with silver oxide ($Ag_2O$) and subsequently recovered as methyl esters.

Particularly interesting results were obtained in the hydroformylation of the styrene and of the isoprene. Also in this case it is impossible to foresee the configuration of the prevailing enantiomer.

C. Asymmetric hydrocarbalkoxylation of prochiral substrata.

Processes as above defined were already performed by using palladium complexes as the catalysts and chiral phosphines as ligands. Also in this case the values of asymmetric induction were always unsatisfactory (never higher than 68%), which, anyhow, did not depend on the used substratum.

We have now discovered in a third representative experiment that the hydrocarbalkoxylation of olefins, employing the new catalytic systems according to the present invention, comprising the conventional palladium complexes and the new ligands, a very high regioselectivity towards the chiral compounds was achieved, and this is absolutely interesting from an industrial point of view, also if noteworthy improvements in the reaction stereospecificity are not observed.

The new catalytic systems gave very interesting results in particular in the synthesis of 2-aryl-propionic acids which are, notoriously widely used antiinflammatory drugs.

The process runs according to the following scheme:

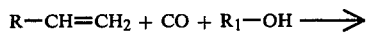

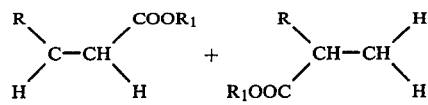

wherein R represents an aliphatic straight or branched group from 1 to 20 carbon atoms or a substituted or unsubstituted aryl group, $R_1$ represents an aliphatic straight or branched group from 1 to 6 carbons.

The hydrocarbalkoxylation process is carried out in autoclave, by dissolving the substratum, the catalyst and the alcohol in an inert organic solvent, preferably an aromatic or aliphatic hydrocarbon, more preferably benzene, and then introducing carbon monoxide until a pressure of 140 atmosphere is reached, at room temperature. The autoclave is then heated at a temperature comprised between 80° C. and 120° C., and the heating is stopped when the gas absorption ceases. The reaction derivatives are collected by distillation after evaporation of the solvent and are further purified by rectification. Particularly suitable catalytic precursors to be used together with the steroidal phosphinic ligands according to the invention are: $PdCl_2$, $Pd(PPh_3)_2Cl_2$, $Pd(OCOCH_3)_2$, $Pd(PhCN)_2Cl_2$ and the like.

The following examples are provided for with the purpose of better illustrating the various aspects of the invention, but in no way they must be construed as a limitation of the scope of the invention itself.

EXAMPLE 1

3α-diphenylphosphine-5α-cholestane ((+)-DICOL)

A solution of 25 g (0.046 moles) of 5α-cholestan-3β-ol tosylate, obtained from cholesterol according to E. B. Hershberg et al., J. Am. Chem. Soc. 73, 1144, (1951) and J. Maunowicz et al., Chem. Listy 52, 2359 (1958), in a 2:1 (v/v) mixture of anhydrous dioxane/tetrahydrofuran was added dropwise, under nitrogen atmosphere, to a solution of sodium diphenylphosphine in 150 ml of a 2:1 (v/v) mixture of anhydorus dioxane/tetrahydrofuran. The sodium diphenylphosphine was obtained in situ from 14.13 g (0.064 moles) of chlorodiphenylphosphine and 7.06 g (0.307 atoms) of metal sodium according to H. B. Kagan et al., J. Am. Chem. Soc. 94, 6429, (1972).

The reaction mixture was stirred at ambient temperature for a period of time of 72 hours and, after addition of 50 ml of diethyl ether, filtered in order to eliminate the inorganic salts. The solvent was evaporated off under vacuum and the residue was taken up with 200 ml of diethyl ether and again filtered. The filtrate was then added with 120 ml of methanol and the resulting mixture was evaporated until a precipitation of a solid product was achieved. After recrystallization from a mixture of diethyl ether and methanol, 15.8 g of product were obtained, with a yield of 60%, calculated over the starting tosylate.

The physical-chemical properties of the compound were as follows:

m.p. 129° C.÷131° C.;

$^1$H-NMR: most significant resonance peaks were observed at 7.62–7.12 p.p.m. (multiplet, 10H, aromatic) and at 2.81–2.5 p.p.m. (multiplet, 1H, H in 3-position)

Mass Spectrum M+ 556 (Relative intensity (Rel. int.) 100%)

$[\alpha]_D^{20} = +22°.0$ (C=0.986 in dioxane)

All these data are in accordance with the compound of formula (II), (+)-DICOL.

EXAMPLE 2

2,3-O-(5'α-cholestanylidene-3',3'-dioxy)-1,4-bis-diphenylphosphinobutane ((−)-DIOCOL 50 Grams (0.13 moles) of 5-cholestan-3-one, prepared from cholesterol according to L. F. and M. Fieser, Org. Synth. Coll. II, 139, were dissolved in 4000 ml of anhydrous benzene together with 100 ml (0.58 moles) of L(+)-diethyl tartrate and 100 mg of p-toluene-sulfonic acid and the resulting mixture was refluxed for 18 hours. After the theoretical amount of water formed, the solution was cooled, neutralyzed and evaporated under vacuum to dryness. The residue was taken up with water, filtered and the precipitate was twice crystallized from a mixture of dichloromethane and methanol.

The 2,3-O-(5'α-cholestanylidene)-L-tartrate was obtained, with a yield of 90% of theoretical.

m.p. 103° C.-104° C.;

$[\alpha]_D^{20} = +4°.24$ (C=1 in dioxane);

Mass Spectrum M+ 574 (Rel. int. 21%).

A suspension of 7 g (0.184 moles) of lithium aluminium hydride in 350 ml of anhydrous diethyl ether was added dropwise with a solution of 42 g (0.073 moles) of diethyl-2,3-O-(5'α-cholestanylidene)-L-tartrate in 350 ml of diethyl ether, under an inert atmosphere.

After refluxing for 4 hours, the reaction mixture was cooled and added with 7 ml of water and 7 ml of a 15% aqueous solution of sodium hydroxide.

The inorganic precipitate was filtered and washed with diethyl ether. The filtrates were collected and evaporated to dryness and the obtained residue was crystallized from a mixture of dichloromethane and methanol. A further crystallization from a mixture of diethyl ether and hexane gave the 2,3-O-(5'α-cholestanylidene)-L-treitol having m.p. 199° C.÷200° C., $[\alpha]_D^{20} = +13°.88$ (C=1 in dioxane), Mass Spectrum M+ 490 (Rel. int. 17%) with a yield of 60% of theoretical.

A solution of sodium diphenylphosphine in a mixture of dioxane and tetrahydrofuran was added dropwise, under stirring at ambient temperature under nitrogen atmosphere, with a solution, in anhydrous tetrahydrofuran, of 23.4 g (0.0295 moles) of 2,3-O-(5'α-cholestanylidene)-L-treitol-1,4-bis-p-toluenesulfonate, obtained with a 95% yield by treating the above 2,3-O-(5'α-cholestanylidene)-L-treitol with p-toluenesulfonyl-chloride in pyridine. The solution was kept under stirring for 48 hours and then poured dropwise in 50 ml of anhydrous ethanol. The solvents were evaporated off in vacuo and the residue, taken up with water, was filtered. The solid was washed with ethanol, dried under vacuum and then dissolved in anhydrous diethyl ether and dried over anhydrous sodium sulphate. After a crystallization from a mixture of diethyl ether and ethanol, 22 g, (90% of theoretical), of pure product were obtained, having the following physical-chemical properties;

m.p. 137° C.÷140° C.;

¹H-NMR shows the most significant peaks at 7.45÷7.05 p.p.m. (multiplet, 20H, aromatic), 3.98÷3.81 p.p.m. (multiplet, 2H, CHO) and 2.61÷2.15 p.p.m. (multiplet, 4H, CH$_2$-P);

$[\alpha]_D^{25}$ = 17.7 (C=1.51 in dioxane)

All these data are in accordance with the compound of formula (III), (−)-DIOCOL.

EXAMPLE 3

Asymmetric hydrogenation of (Z)-acetylaminocinnamic acid 5 m.moles of (Z)-acetylaminocinnamic acid, 0.05 m.moles of [(COD)RhCl]$_2$ (cyclooctadienyl rhodium chloride dimer) and 0.055 m.moles of (−)-DIOCOL were poured into 250 ml stainless steel autoclave.

After removing the air by means of a mechanical pump, 40 ml of a 1:1 (v/v) mixture of benzene and methanol were introduced by suction, the autoclave was filled with 70 atmospheres of hydrogen and subsequently kept under stirring overnight at ambient temperature. Once the reaction was terminated the solvent was evaporated off under vacuum and the residue was taken up with an aqueous 5% sodium bicarbonate solution. The solution was extracted with diethyl ether and the aqueous layer, after separation, was acidified by means of a 10% aqueous solution of hydrochloric acid.

The acidic solution was then throughly extracted with diethyl ether and the organic extract was dried over sodium sulphate. By evaporating off the solvent, 4.5 m.moles of (−)-N-acetyl(R)-phenylalanine were obtained, having $[\alpha]_D^{25}$ = −41°.9 (con.=1 in ethanol), corresponding to an optical purity of 91%.

EXAMPLE 4

Asymmetric hydrogenation of (E)-β-methylcinnamic acid

By operating substantially according to the procedure of Example 3, the (−)-(R)-3-phenylbutanoic acid was obtained, with a yield of 92%, having $[\alpha]_D^{25}$ = −4°.77 (C=6 in chloroform), corresponding to an optical purity of 10.8%, starting from the (E)-β-methylcinnamic acid ((E)-3-phenyl-2-butanoic acid).

EXAMPLE 5

Asymmetric hydrogenation of the mesaconic acid

By operating substantially according to the procedure of Example 3, the (+)-(R)-methylsuccinic acid was obtained, with a yield of 70%, having $[\alpha]_D^{25}$ = +1°.15 (C=4.68 in ethanol), corresponding to an optical purity of 9.2%, starting from (E)-methyl-2-butenedioic acid (mesaconic acid).

EXAMPLE 6

Asymmetric hydrogenation of the methyl ester of the (Z)-acetylaminocinnamic acid The hydrogenation reaction was carried out substantially as described in Example 3. The reduction product was isolated according to the following procedure.

The reaction mixture, after evaporating off the solvent under vacuum, was dissolved in 15 ml of diethyl ether and filtered through a cromatographic column containing a 3 cm thickness of silica gel. By evaporating off the filtrate (−)-N-acetyl-(R)-phenylalanine methyl ester was obtained, with a yield of 75%, having $[\alpha]_D^{25}$ = −2°.78 (C=2 in methanol), corresponding to an optical purity of 18%.

EXAMPLE 7

Asymmetric hydrogenation of (Z)-acetylaminocinnamic acid 5 m.moles of (Z)-acetylaminocinnamic acid, 0.05 m.moles of [(COD)RhCl]$_2$ and 0.11 m.moles of (+)-DICOL were poured into a 250 ml stainless steel autoclave.

After removing the air by means of a mechanical pump, 40 ml of a 1:1 (v/v) mixture of benzene and methanol were introduced by suction, the autoclave was filled with 70 atmospheres of hydrogen and subsequently kept under stirring overnight at ambient temperature. Once the reaction was terminated, the solvent was evaporated off under vacuum and the residue was taken up with an aqueous 5% sodium bicarbonate solution.

The solution was extracted with diethyl ether and the aqueous layer, after separation, was acidified by means of a 10% aqueous solution of hydrochloric acid. The acid solution was then throughly extracted with diethyl ether and the organic extract was dried over sodium sulphate. By evaporating off the solvent, 4.8 m.moles of almost racemic N-acetylphenylalanine were obtained with a yield of 96% of theoretical.

EXAMPLE 8

Asymmetric hydrogenation of (E)-β-methylcinnamic acid

By operating substantially according to the procedure of Example 7, almost racemic 3-phenylbutanoic acid was obtained with a yield of 96%, starting from (E)-β-methylcinnamic acid.

EXAMPLE 9

Asymmetric hydroformylation of 1-butene $1 \times 10^{-4}$ Moles of HRh(CO)(PPh$_3$)$_3$ and $3 \times 10^{-4}$ moles of (+)-DICOL were introduced into a 0.2 liters stainless steel autoclave. The air was then removed by means of a mechanical pump, 40 ml of mesitylene were introduced by suction and finally, after cooling the autoclave to −30° C., the reaction mass was added with 0.1 moles of 1-butene. The autoclave was loaded with an equimolecular mixture of carbon monoxide and hydrogen at ambient temperature, reaching a pressure of 90 atmospheres, and the whole was subsequently heated to 60° C. by means of an oil bath. The practically complete (99%) convertion of the starting substratum was achieved in 16 hours. The 2-metylbutanal was obtained as the sole product of the hydroformylation with a yield of 90% by rectifying the reaction mixture. The optical purity of the obtained aldehyde was determined by oxidizing it with silver oxide and sodium hydroxide to the corresponding 2-methylbutanoic acid and by measuring its optical activity: the prevailing enantiomer showed an (S) configuration and the enantiomeric excess was 1%.

The reaction conditions and the results obtained in the asymmetric hydroformylation (carried out substantially as described in this example) of olefin hydrocarbons in the presence of the catalytic system HRh(CO)(PPh$_3$)$_3$/(+)-DICOL are shown in the following Table 1.

The data related to the conditions and the obtained results in asymmetric hydroformylation of various substrata by using a catalytic system comprising (−)-DIOCOL have been collected in Table 2.

starting substratum was transformed into esters. By means of a fractional distillation a mixture of esters was obtained, with a yield of 80%, containing 11.4% of methyl (R)-2,3,3-trimethylbutanoate having an optical

TABLE 1

Asymmetric hydroformylation of olefins carried out with (+)-DICOL as the chiral ligand
Substratum: 0.1 moles; benzene: 40 ml;
HRh(CO)(PPh₃)₃/olefin ≃ 1/500
HRh(CO)(PPh₃)₃/(+)-DICOL = ½
$P_{tot}$. 80–90 atm. at ambient temperature; CO/H₂ = 1/1

| SUBSTRATUM | React. temp. °C. | React. time hours | Conversion % | Yield % | Optically active compound Name | A | % ee | (CONF) |
|---|---|---|---|---|---|---|---|---|
| Cis-butene | 80 | n.d | 99 | 91 | 2-methylbutanoic acid | 100 | 0 | |
| 2,5-dihydrofuran | 60 | 30 | 99 | 90 | tetrahydrofuran-3 carboxylic acid | 100 | 0 | |
| styrene | 80 | 4 | 45 | 30 | 2-phenylpropanoic acid | 89 | 1 | (R) |
| 2-phenylpropene | 90 | 110 | 66 | 52 | 3-phenylbutanal | 95 | 1 | (R) |

A = percent of chiral aldehyde in the reaction product
ee = enantiomeric excess

TABLE 2

Asymmetric hydroformylation of olefins carried out with (−)-DIOCOL as the chiral ligand.
Substratum: 0.1 moles; benzene: 40 ml
HRh(CO)(PPh₃)₃/olefin ≃ 1/500
HRh(CO)(PPh₃)₃/(−)-DIOCOL = 1/1.5
$P_{tot}$. 80–90 atm. at ambient temperature; CO/H₂ = 1/1

| SUBSTRATUM | React. temp. °C. | React. time hours | Conversion % | Yield % | Optically active compound Name | A | % ee | (CONF) |
|---|---|---|---|---|---|---|---|---|
| 1-butene | 60 | 65 | 98 | 91 | 2-methylbutanoic acid | 13 | 3.8 | (R) |
| Cis-butene | 90 | n.d. | 98 | 90 | 2-methylbutanal | 100 | 1 | (S) |
| 2,5-dihydrofuran | 60 | 44 | 99 | 93 | tetrahydrofuran 3-carboxylic acid | 100 | 3.3 | (R) |
| 2,3,3-trymethyl-1-butene | 100 | n.d. | 65 | 50 | 3,4,4-trimethyl pentanoic acid | 100 | 1.1 | (R) |
| styrene | 80 | 16 | 92 | 85 | 2-phenylpropanoic acid | 68 | 6.3 | (R) |
| 2-phenylpropene | 90 | 240 | 55 | 50 | 3-phenylbutanal | 95 | 1 | (S) |
| isoprene | 80 | 140 | 98 | 30 | 3-methylpentanoic acid | — | 34.2 | (S) |

A = percent of chiral aldehyde in the reaction product
ee = enantiomeric excess

EXAMPLE 10

Asymmetric hydrocarbomethoxylation of 3,3-dimethyl-1-butene 8.4 Grams (0.1 moles) of 3,3-dimethyl-1-butene, 50 ml of a 4:1 (v/v) mixture of benzene/methanol, 35 mg (2×10⁻⁴ moles) of palladium chloride and 223 mg (4×10⁻⁴ moles) of (+)-DICOL were introduced into a 0.2 liters stainless steel autoclave. The reaction vessel was loaded with carbon monoxide at 100 atmospheres and then heated for 47 hours at 70° C. The 93% of the starting substratum was transformed into esters. By means of a fractional distillation a mixture of esters was obtained, with a yield of 80%, containing 11.4% of methyl (R)-2,3,3-trimethylbutanoate having an optical purity of 2.6%.

The reaction conditions and the results of other experiments of asymmetric hydrocarbalkoxylation carried out according to the hereinbefore described process in the presence of palladium chloride and (+)-DICOL as the catalytic system have been summarized in the following Table 3.

The reaction conditions and the results obtained in the hydrocarbethoxylation of various substrata by using the catalytic system containing (−)-DIOCOL have been summarized in Table 4.

TABLE 3

Hydrocarbalkoxylation of olefins carried out by means of (+)-DICOL as the chiral ligand.
Substratum: 0.1 moles; benzene/ethanol = 4/1
PdCl₂/olefin ≃ 1/500; PdCl₂/(+)-DICOL = ½

| SUBSTRATUM | React. temp. °C. | React. time hours | $P_{CO}$ atm. | Conv. % | Yield % | Optically active compound name | A | % ee | (CONF) |
|---|---|---|---|---|---|---|---|---|---|
| 1-butene | 70 | 18 | 140 | 80 | 65 | ethyl 2-methyl-butanoate | 58.6 | 2 | (S) |
| Cis-butene | 70 | 41 | 140 | 85 | 72 | ethyl-2-methyl-butanoate | 98.5 | 1 | (R) |
| 2,3,3-trimethyl- | 100 | 164 | 80 | n.d. | 33 | ethyl-3,4,4- | 100 | 2.5 | (R) |

TABLE 3-continued

| | | | | | | | | | |
|---|---|---|---|---|---|---|---|---|---|
| 1-butene | | | | | | trimethyl-pentanoate | | | |
| styrene | 80 | 96 | 90 | 99 | 9 | ethyl 2-phenyl-propanoate | 100 | 1.6 | (S) |
| phenylpropene | 100 | 24 | 95 | 85 | — | — | 0 | — | |

A = percent of chiral aldehyde in the reaction product
ee = enantiomeric excess e

TABLE 4

Hydrocarbalkoxylation of olefins carried out by means of (−)-DIOCOL as the chiral ligand
Substratum: 0.1 moles; benzene/ethanol = 4/1
$PdCl_2$/olefin = 1/500; $PdCl_2$/(−)-DIOCOL = 1/1

| SUBSTRATUM | React. temp. °C. | React. time hours | $P_{CO}$ atm. | Conv. % | Yield % | Optically active compound name | A | % ee | (CONF) |
|---|---|---|---|---|---|---|---|---|---|
| 1-butene | 90 | 15 | 150 | 98 | 88 | ethyl 2-methyl-butanoate | 27 | 4.3 | (S) |
| Cis-butene | 100 | 12 | 140 | 99 | 91 | ethyl-2-methyl-butanoate | 59.3 | 2.1 | (R) |
| 2,3,3-trimethyl-1-butene | 100 | 72 | 80 | 75 | 68 | ethyl-3,4,4-trimethyl-pentanoate | 100 | 12.5 | (S) |
| 2-phenylpropene | 120 | 24 | 80 | 99 | 95 | ethyl 3-phenyl butanoate | 100 | 1.3 | (S) |
| styrene | 70 | 47 | 100 | 99 | 80 | ethyl 2-phenyl propanoate | 44 | 6.7 | (S) |

A = percent of chiral aldehyde in the reaction product
ee = enantiomeric excess

We claim:

1. New steroidal chiral phosphines of formula:

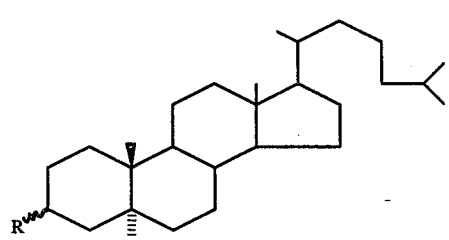

(I)

wherein R represents a phosphorated group selected between

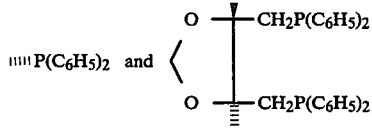

2. A compound as defined in claim 1, of formula:

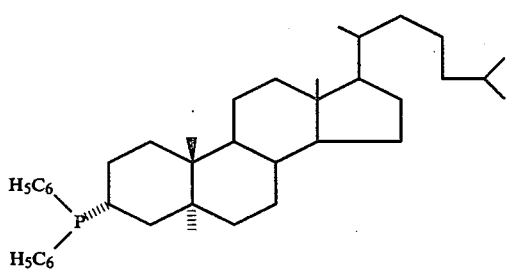

(II)

3. A compound as defined in claim 1, of formula:

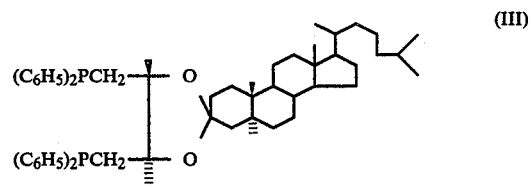

(III)

4. A process for preparing a steroidal chiral phosphine of formula

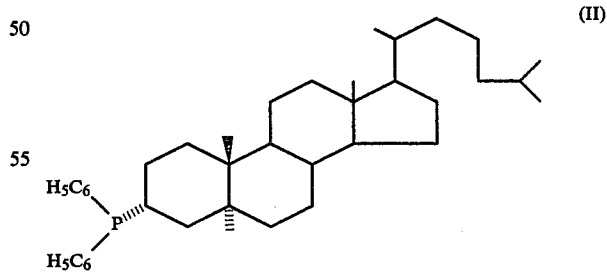

(II)

which comprises reacting the 5α-cholestane-3β-ol tosylate with sodium diphenylphosphine under nitrogen atmosphere in an anhydrous inert organic solvent like dioxane or tetrahydrofuran or mixtures thereof, at room temperature for a period of time comprised between 2 and 4 days.

5. A process for preparing a steroidal chiral phosphine of formula:

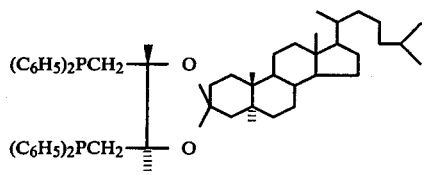
(III)

which comprises reacting the 5α-cholestane-3-one with (R)(R)-diethyl tartrate in an inert organic solvent like toluene or benzene in th presence of p-toluenesulfonic acid, at the boiling temperature of the reaction mixture for a period of time comprised between 12 and 24 hours, reducing the carbethoxy groups to hydroxymethyl groups by means of a metal hydride like lithium aluminium hydride or sodium borohydride in anhydrous diethyl ether at the boiling temperature of the reaction mixture for a period of time comprised between 2 and 10 hours, protecting the hydroxy groups by reaction with p-toluenesulfonyl chloride and reacting the so obtained p-toluenesulfonyl derivative with sodium diphenylphosphine under stirring at room temperature, in an inert organic solvent like dioxane, tetrahydrofuran or a mixture thereof, for a period of time comprised between 24 and 72 hours.

* * * * *